United States Patent [19]

France et al.

[11] Patent Number: 5,063,916
[45] Date of Patent: Nov. 12, 1991

[54] KNEE BRACE HAVING FREECENTRIC LOCKING HINGE

[75] Inventors: E. Paul France, Salt Lake City; Richard L. Ellingson, Draper; Lonnie E. Paulos, Salt Lake City, all of Utah

[73] Assignee: Minnesota Mining and Manufacturing Company, St. Paul, Minn.

[21] Appl. No.: 531,927

[22] Filed: Jun. 1, 1990

[51] Int. Cl.[5] .............................................. A61F 3/00
[52] U.S. Cl. .................................. 128/80 C; 128/80 F
[58] Field of Search ................. 128/80 C, 80 R, 84 R, 128/88, 123.1, 80 F; 16/357, 361, 362, 363

[56] References Cited

U.S. PATENT DOCUMENTS

| | | | |
|---|---|---|---|
| 1,622,211 | 3/1927 | Sheehan | 128/80 C |
| 3,387,305 | 6/1968 | Shafer | 128/80 C |
| 3,528,412 | 9/1970 | McDavid | 128/80 C |
| 3,745,997 | 7/1973 | Gledhill | 128/88 |
| 3,779,654 | 12/1973 | Horne | 128/80 C |
| 3,902,482 | 9/1975 | Taylor | 128/80 F |
| 4,245,629 | 1/1981 | Cummins | 128/80 C |
| 4,323,059 | 4/1982 | Rambert et al. | 128/88 X |
| 4,506,661 | 3/1985 | Foster | 128/80 C |
| 4,554,913 | 11/1985 | Womack et al. | 128/88 X |
| 4,637,382 | 1/1987 | Walker | 128/902 |
| 4,655,201 | 4/1987 | Pirmantgen | 128/80 C |
| 4,691,697 | 9/1987 | Arensdorf et al. | 128/80 L |
| 4,723,539 | 2/1988 | Townsend | 128/80 C |
| 4,768,500 | 9/1988 | Mason et al. | 128/80 C |
| 4,791,916 | 12/1988 | Paez | 128/80 C |
| 4,821,707 | 4/1989 | Audette | 128/80 C X |
| 4,890,607 | 1/1990 | Townsend | 128/80 C |
| 4,953,543 | 9/1990 | Grim et al. | 128/80 C |
| 4,955,369 | 9/1990 | Bledsoe et al. | 128/80 C |

Primary Examiner—Richard J. Apley
Assistant Examiner—J. Doyle
Attorney, Agent, or Firm—Berne S. Broadbent

[57] ABSTRACT

The present invention relates to a knee brace which includes an upper and lower cuff which are attached at the medial and lateral sides of the knee joint by freecentric locking hinges. The freecentric hinge includes a free floating center of rotation which allows simultaneous translation and rotation of the upper hinge arm relative to the lower hinge arm. The freecentric hinge may further include a locking mechanism which comprises a pin located on the upper hinge arm and a hook located on the lower hinge arm which may be forced into engagement to prevent further rotation of the hinge when it is desired to prevent hyperextension of the user's knee. A pair of tension straps may be attached across the back of the user's knee from the upper cuff to the lower cuff, and adjusted in its length so that extension of the knee tends to generate tension in the strap which aids in pulling the upper and lower cuff members to be pulled towards each other. The motion of the upper and lower cuffs toward each other causes the hook and pin of the locking mechanism to be correctly positioned for interengagement and locking of the hinge against further extensional rotation. If desired, the upper hinge arm may be attached to the upper cuff in a manner which allows free sliding movement therebetween in order to compensate for forces incident on the brace due to the motion of the hinge as it tracks the rotation of the user's knee.

11 Claims, 8 Drawing Sheets

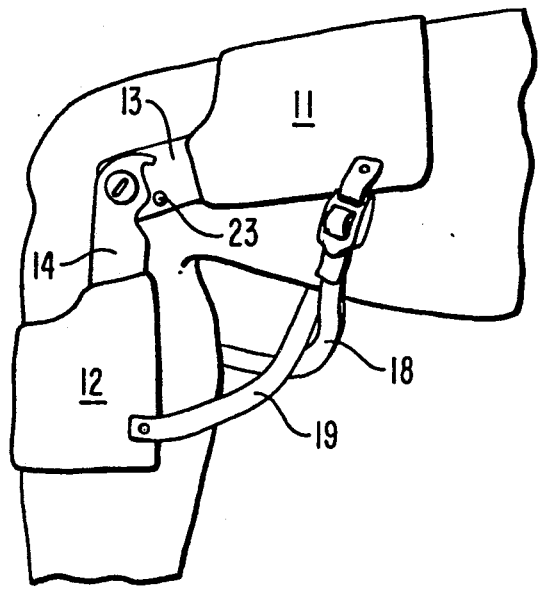
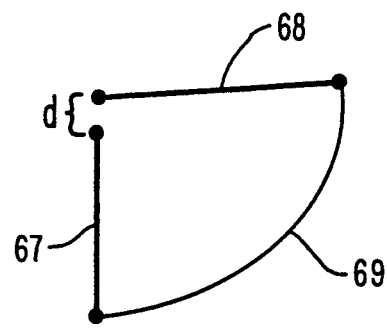
FIG. 6a
FIG. 6b
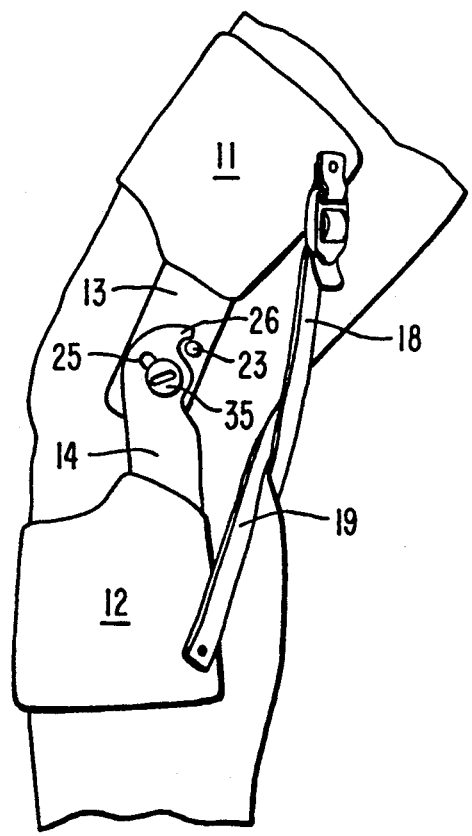
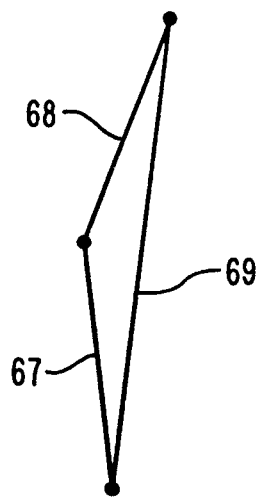
FIG. 7a
FIG. 7b

KNEE BRACE HAVING FREECENTRIC LOCKING HINGE

BACKGROUND OF THE INVENTION

1. Field of the Invention

The present invention relates to a knee brace, and more specifically relates to a knee brace incorporating at least one locking hinge having a free floating center of rotation.

2. Prior Art

Braces are often utilized to support the knee when damage, deformation, surgery, or the like has caused the knee to be instable. Most often, a knee brace is used to protect the knee against further injury and/or to provide extra support for a previously injured knee during periods of activity such as when the user walks, runs or participates in athletic events.

Prior art knee braces have taken a variety of different forms and complexities. Knee braces have in the past been as simple as a wrapping of materials such as an elasticized band around the knee joint. Such wrappings, although causing a loss of mobility, nevertheless strengthen the joint to some degree. Complex and/or rigid knee braces, including casts or other completely immobilizing devices have also been used in the past. In between these extremes, there are numerous devices which are attached to the upper and lower leg and include hingeable members located at the knee joint. These types of braces are intended to provide some sort of support for the knee while attempting to preserve maximum mobility.

It has been known in knee braces of the last mentioned type to include structural features in the hinging portions thereof which prevent the knee joint from being hyperextended. Further, it is known in this type of prior art brace to include structural elements which cause the rotational motion of the hinge to somewhat imitate the hinging motion of the knee joint itself.

Knee braces incorporating the above-mentioned concepts are exemplified by the U.S. Pat. No. 4,791,916 to Paez. Paez discloses a knee brace having upper and lower cuffs which are attached respectively to the upper and lower portions of the leg above and below the knee. The cuffs are attached so as to orient a pair of polycentric hinges adjacent the medial and lateral sides of the knee in order to control the extent of leg flexion and extension.

It has in the past been very difficult to incorporate a polycentric type hinge into a knee brace which is also capable of preventing hyperextension of the knee. This is because the design necessary to track the hinging motion of the knee joint becomes complicated with the incorporation therein of a locking mechanism. This has been because the structural elements necessary to cause the hinge to lock in a predetermined position to prevent further hinging motion, tends to interfere with the rotational capabilities of the hinge.

Prior art devices which attempt to incorporate a locking mechanism into a polycentric type hinge for limiting the hinge's pivoting motion to prevent hyperextension of the patients knee, have in the past had an added problem of maintaining desired positioning on the user's leg. This is because these types of knee braces tend to slide upward or downward on the user's thigh during motion of the knee due to ineffectiveness of the brace in duplicating the leg's hinging motion. Forces generated by the engagement of a locking mechanism in the brace's hinge also tend to cause slippage of the brace. Brace slippage upward or downward on the user's leg, causes the brace's hinges to move from their correct position at the sides of the knee, which in turn causes the brace to misfunction. Sometimes this slippage, if extensive, can even render the brace hazardous to the patient.

SUMMARY OF THE INVENTION

It is an object of the present invention to provide a knee brace having a hinge which is of simple design and construction yet which accurately tracks the hinging motion of the knee.

It is another object of the present invention to provide a knee brace having a hinge which can include a locking mechanism if desired which will automatically lock the motion of the hinge at a predetermined extended position in order to prevent hyperextension of the user's knee.

It is further an object of the present invention to provide a knee brace which can include an upper immobilization cuff which is slidably attached to its upper hinge arms in order to improve the ability of the knee brace to maintain its desired position on the leg when in use.

These and other objects of the present invention are realized in a knee brace having upper and lower cuffs which are attachable to the thigh and lower leg respectively of a user by means of upper and lower immobilization bands. The upper cuff of the brace has a pair of hinge arms which extend downwardly to positions directly adjacent the lateral and medial sides of the user's knee, each upper hinge arm containing a slot at its distal end which is angled approximately 45 degrees from the longitudinal axis of the upper hinge arm, and a locking pin located between the slot and the point of connection between the upper cuff and the hinge arm. Each lower cuff also includes a pair of lower hinge arms which extend upwardly so as to be located adjacent each side of the knee and to overlap the upper hinge arms, each lower hinge arm including a slot angled approximately 45 degrees from a longitudinal axis of the lower hinge arm, and angled approximately 90 degrees from the slot in the upper hinge arm when upper and lower hinge arms are approximately longitudinally aligned. The slots of the upper and lower hinge arms are held in rotatable, overlapping relationship by a shielded washer and screw. The lower hinge arms each included a hook member which will engage the locking pin on the upper hinge arm prior to hyperextension of the knee (for preventing further hinging motion of the knee brace, and subsequently of the knee joint itself, past a predetermined extended position). The lower cuff further includes a pair of cross straps which are located at opposite sides of the lowermost portion of the lower cuff and which extend around the back of the user's leg to attach to a pair of fastening members located at the sides of the uppermost portion of the upper cuff. The cross straps cross each other at the back of the user's leg directly behind the knee, and tend to tighten as the user's leg is extended. Extension of the knee thereby pulls the lower cuff into closer proximity to the upper cuff as the user's leg straightens. Continuance of the extension motion causes the upper and lower hinge arms to move towards each other as far as the slots (and screw attached therethrough) will allow.

The continued extension of the user's leg eventually causes the lower hinge arm hook to move upwardly a sufficient distance to be engageable with the locking pin on the upper hinge arm. Extensional rotation to the point where the hook engages the locking pin renders further hinging movement of the knee brace impossible, thus preventing hyperextension of the knee. Movement of the leg in the opposite direction (to cause flexion of the knee joint) allows the hook to disengage with the locking pin and also allows the cross straps to gradually become slack, thereby returning freedom of movement to the hinging elements of the brace. The free movement allows the freecentric hinge to track the rotational motion of the knee without interference from the hook and pin locking mechanism. The upper and lower cuffs of the brace include immobilization bands which retain them in their proper position on the leg.

In a second embodiment of the present invention, a pair of channels may be included in the upper cuff thereof, into which the upper hinge arms can be inserted and slidably held in a pin-and-slot relationship therewith. The upper hinge arms are therefore attached to the upper cuff of this embodiment in a slidable relationship rather than in rigid relationship as in the above embodiment. The relative movement between the upper hinge arms and the upper cuff during use of this embodiment of the invention allows a greater range of motion of the leg with greater comfort to the user, and prevents upward or downward slippage of the upper cuff of the brace on the user's thigh. If desired, the upper hinge arms may be used in conjunction with prior art knee braces. In such a case, the hinge arm may alternatively be slidably attached to the hinge member if desired, rather than to the cuff.

BRIEF DESCRIPTION OF THE DRAWINGS

The aforementioned objects and advantages of the present invention will be appreciated from the following description and accompanying drawings in which like numerals represent like structural features in each drawing, wherein:

FIG. 5b is an expanded view of the freecentric locking hinge shown in FIG. 5a;

FIG. 6a is a side view of a leg having the knee brace of the present invention attached thereto (the immobilization bands being omitted for clarity) with the knee at 90 degrees flexion;

FIG. 6b is a schematic showing the relative positions of elements of the knee brace of FIG. 6a;

FIG. 7a is a side view of a leg having the knee brace of the present invention attached thereto (the immobilization bands being omitted for clarity) with the knee approaching full extension;

FIG. 7b is a schematic showing relative positions of elements of the knee brace of FIG. 7a;

DETAILED DESCRIPTION OF THE INVENTION

Figure 1:
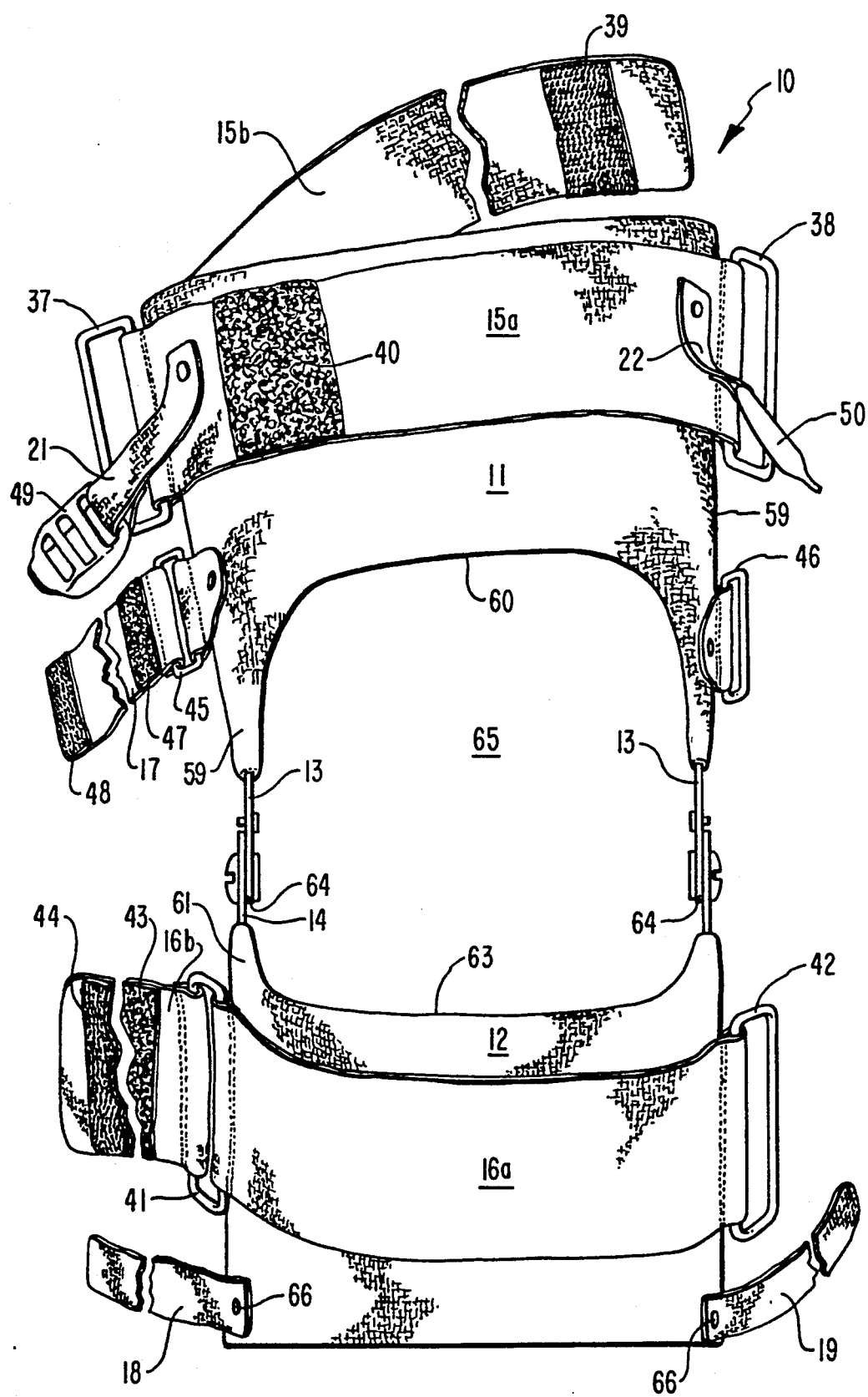
FIG. 1 is a front view of a knee brace constructed in accordance with the principles of the present invention.
Figure 2:
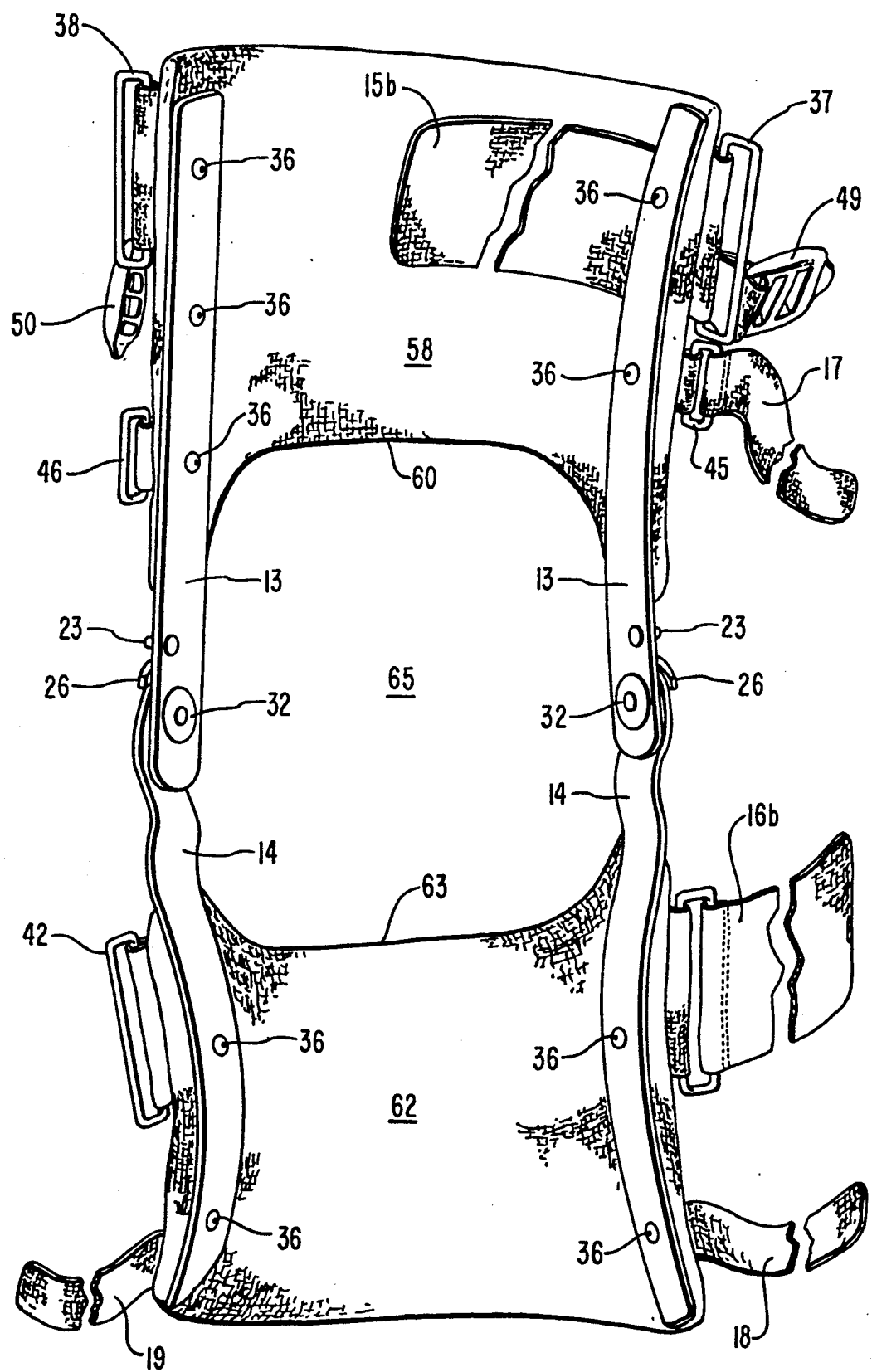
FIG. 2 is a rear view of a knee brace constructed in accordance with the principles of the present invention.
Figure 3:
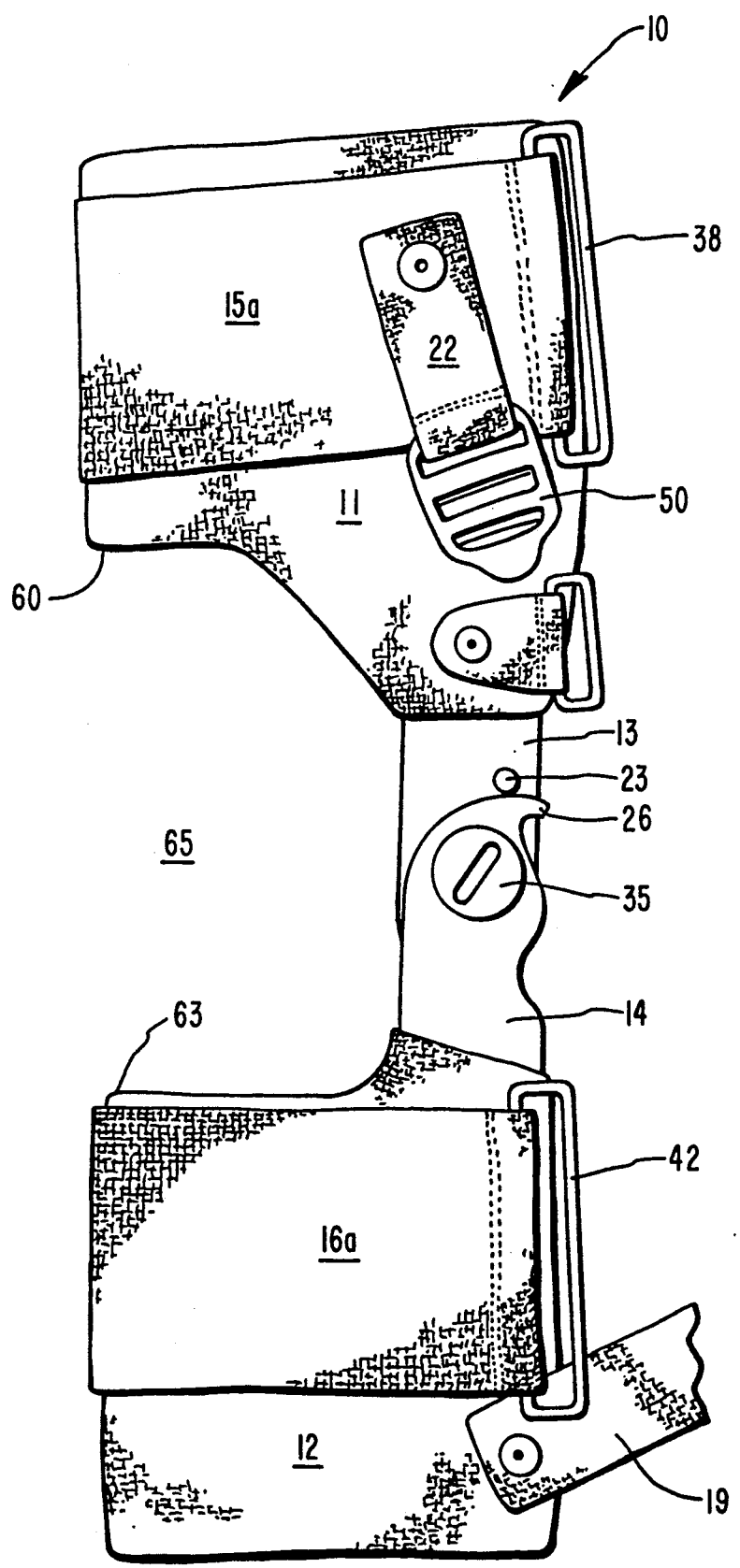
FIG. 3 is a side view of a knee brace constructed in accordance with the principles of the present invention.

FIG. 1 shows a front view of a knee brace 10 constructed according to the principles of the present invention. The brace 10 includes an upper cuff 11 of a generally U-shaped configuration. The upper cuff 11 is formed preferably of a relatively rigid material such as metal, wood, plastic, fiberglass, graphite or other composite material. The interior surface 58 of the U-shaped cuff 11 may be padded if desired with a soft, woven or similar type material. The configuration of the U-shaped upper cuff 11 is intended to match the shape of the thigh of the user and is intended to extend approximately halfway around a user's leg beginning from the interior (medial) side thereof around the thigh to the exterior (lateral) side.

The lower cuff 12 is quite similar in materials and configuration to the upper cuff 11 except that it is of smaller dimensions so as to closely fit over the shin area of the lower leg of the user. The lower cuff 12 is shaped to match the shin area of a user's leg, and is also intended to extend approximately around the front half of the user's lower leg as explained above with respect to the upper cuff 11.

The lower edge 60 of the upper cuff 11, and the upper edge 63 of the lower cuff 12, are cut away to form a generally oval opening 65 therebetween inside which the knee joint may freely flex without interference from the brace 10.

A pair of upper hinged arms 13 are connected, one each, adjacent the side edges 59 of the U-shaped cuff 11 and extend below the lower edge 60 thereof so as to be located adjacent the lateral and medial sides of the user's knee. The hinge arms 13 extend along the interior surface 58 adjacent the edge 59 of the cuff 11 in approximately parallel relationship, and protrude below the lower edge 60 of the cuff 11 so as to be located one on each side of the knee when the cuff 11 is attached to a user's leg.

Similarly, the lower cuff 12 has a pair of lower hinge arms 14, one each respectively located adjacent the side edges 61 of the U-shaped lower cuff 12. Each lower hinge arm 14 extends along the interior surface 62 of the lower cuff 12 adjacent the edges 61 in approximately parallel relationship, with each arm 14 extending above the upper edge 63 of the cuff 12 a distance sufficient to be located, one each, at the lateral and medial sides of the user's knee when the lower cuff 12 is correctly positioned about the shin, and also so as to overlap the distal ends 64 of the upper hinge arms 13.

The upper and lower hinge arms 13 and 14 respectively, are interconnected by means of a shielded washer 31 and screw 34, (see FIG. 5b) for freecentric pivotal movement through a predetermined range of motions. The term "freecentric" is used in context of the present invention to describe the hinging action, or rotational motion, of the hinge arms 13 and 14, and is defined as "a rotational motion about free floating centers of rotation". The freecentric hinging action of the present invention is thus distinguished from the "multiple, fixed centers of rotation" of a "polycentric" type hinge. The freecentric hinging action of the present invention is made possible by the completely "free floating" nature of the shielded washer 31 in the slots 24 and 25 of the upper and lower hinge arms 13 and 14 as will be explained below.

Figure 5A:
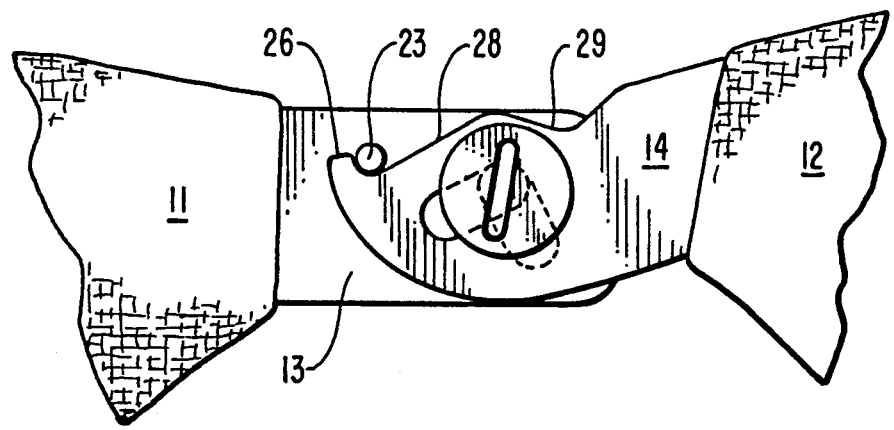
FIG. 5a is an enlarged view of the freecentric locking hinge constructed in accordance with the principles of the present invention.
Figure 5B:
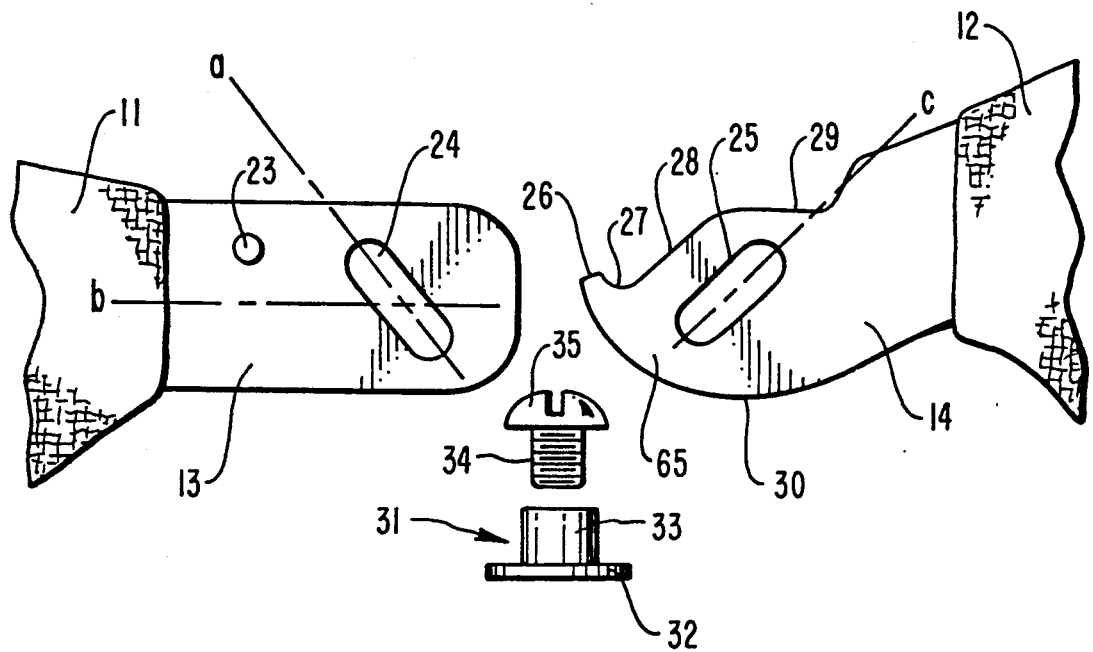

As best seen in FIGS. 5a and 5b, each upper hinge arm 13 includes a slot 24 formed in its distal end 64 which is of a length approximately 2 to 2½ times its width. The slot 24 is formed in the upper hinge arm 13 so that its longitudinal axis (a) is at approximately a 45 degree angle from the longitudinal axis (b) of the upper hinge arm 13 itself.

Each lower hinge arm 14 includes a slot 25 formed in its distal end 65 which is of approximately the same dimensions as the upper hinge arm slot 24. The lower hinge arm slot 25 is oriented such that its longitudinal axis (c) is at a angle of approximately 90 degrees from the longitudinal axis (a) of the upper hinge arm slot 24, when the upper and lower hinge arms 13 and 14 are oriented in their locked position (see FIG. 5a).

The upper and lower hinge arms 13 and 14 are rotatably connected by means of the screw 34 and shielded washer 31. The shield 33 of the washer 31 includes interior threads (not shown). The shield 33 extends through the upper and lower hinge arm slots 24 and 25 and is threadedly attached to screw 34 such that screwhead 35 rests on the exterior surface of lower hinge arm 14, while the plate 32 of the washer 31 rests on the interior surface of upper hinge arm 13.

The washer 31 and screw 34 are allowed to freely rotate and translate with respect to upper and lower hinges arms 13 and 14 within respective hinge arm slots 24 and 24. Further, each hinge arm 13 and 14 is allowed to freely rotate relative to each other.

Since washer 31 and screw 34 constitute the connector between the upper and lower hinge arms 13 and 14, they also constitute the center of rotation of the hinge arms 13 and 14 relative to each other. Thus, the center of rotation of the hinge arms 13 and 14 is "free floating" as opposed to prior art polycentric hinges which have a plurality of fixed centers of rotation. Further, the center of rotation (washer 31 and screw 34) of the present invention also allows for free translation (linear movement) of each of the hinge arms 13 and 14 relative to the center of rotation, along the longitudinal axis (a) and (c) of slots 24 and 25. This translation can occur at any time, either independent of, or simultaneously with, relative rotation of the hinge arms 13 and 14.

If it is desired to incorporate a locking mechanism into the brace 10, the lower hinge arm 14 may be shaped at its distal end 65 to include a hook 26(as best shown in FIG. 5b). The hook 26 arcuately extends from distal end 65 so as to be engageable under certain circumstances, with locking pin 23 located on upper hinge arm 13 (as shown in FIG. 5a) in the manner, and under the circumstances, as will be explained below. The hook 26 is formed in part by the semi-circularly shaped surface 30 at the distal end 65 of the hinge arm 14, and in part by the semi-circularly shaped surface 27 which contacts the locking pin 23 when the hinge is in its locked position.

The generally straight edge 28 of the hinge arm 14 extends generally parallel to the longitudinal axis (c) of the slot 25 and is formed to prevent its interference with pin 23 when the hinge is rotated due to flexion of the user's knee. Semi-circular indentation 29 is also formed in lower hinge arm 14 and is also necessary to prevent interference of the lower hinge 14 with locking pin 23 during rotation of the hinge.

In use, the brace 10 of the present invention incorporating the above described locking mechanism, is attached to the user's knee by first placing upper cuff 11 about the user's lower thigh. This is done by placing the entire surface 58 thereof directly against the front of the user's thigh in a position slightly above the knee so that hinge arms 13 are located adjacent the medial and lateral sides thereof.

The upper cuff 11 is then secured to the user's thigh by passing portion 15b of the upper immobilization band through D-ring 38, around the back of the user's lower thigh, through D-ring 37, and, changing directions, around the back of the user's leg a second time and over the front portion 15a of the immobilization band 15a to connect hook and loop fastener 39 to its equivalent counterpart fastener 40.

Upper immobilization strap 17, attached to the upper cuff 11 by D-ring 45, is then passed around behind the users leg and, inserted through D-ring 46, and, changing directions, doubled back onto itself until hook and loop fastener 48 is attached to its equivalent counterpart fastener 47.

The lower cuff 12 is then attached about the shin area of the user's leg by passing portion 16b of the lower immobilization band (which is attached to portion 16a by D-ring 41), around the back of the user's shin and through D-ring 42, and, changing direction, doubled back upon itself to attach hook and loop fastener 44 to its equivalent counterpart fastener 43.

Cross-straps 18 and 19 are not intended to be used as fasteners for holding the brace 10 on the user's leg. Instead, cross-straps 18 and 19 are used, if desired, to generate an actuation force for assisting in properly orienting the hook 26 relative to the pin 23 of the locking mechanism for proper locking engagement. Working in conjunction with the slots 24 and 25 in hinge arms 13 and 14 respectively, the cross-straps 18 and 19, when tensioned by extension of the knee, move the hook 26 of the lower hinge arms 14 into locking position with locking pin 23 of upper hinge arm 13. Cross-straps 18 and 19 are attached to lower cuff 12 by rivets 66 or any similar manner. Once the brace 10 is attached to the user's leg, cross-strap 18 is passed behind the user's knee and inserted into fastener 50 which is attached to upper cuff 11 by strap 22. Similarly, cross-strap 19 is passed behind the user's knee and attached to fastener 49 attached to upper cuff 11 by strap 21.

Figure 4:
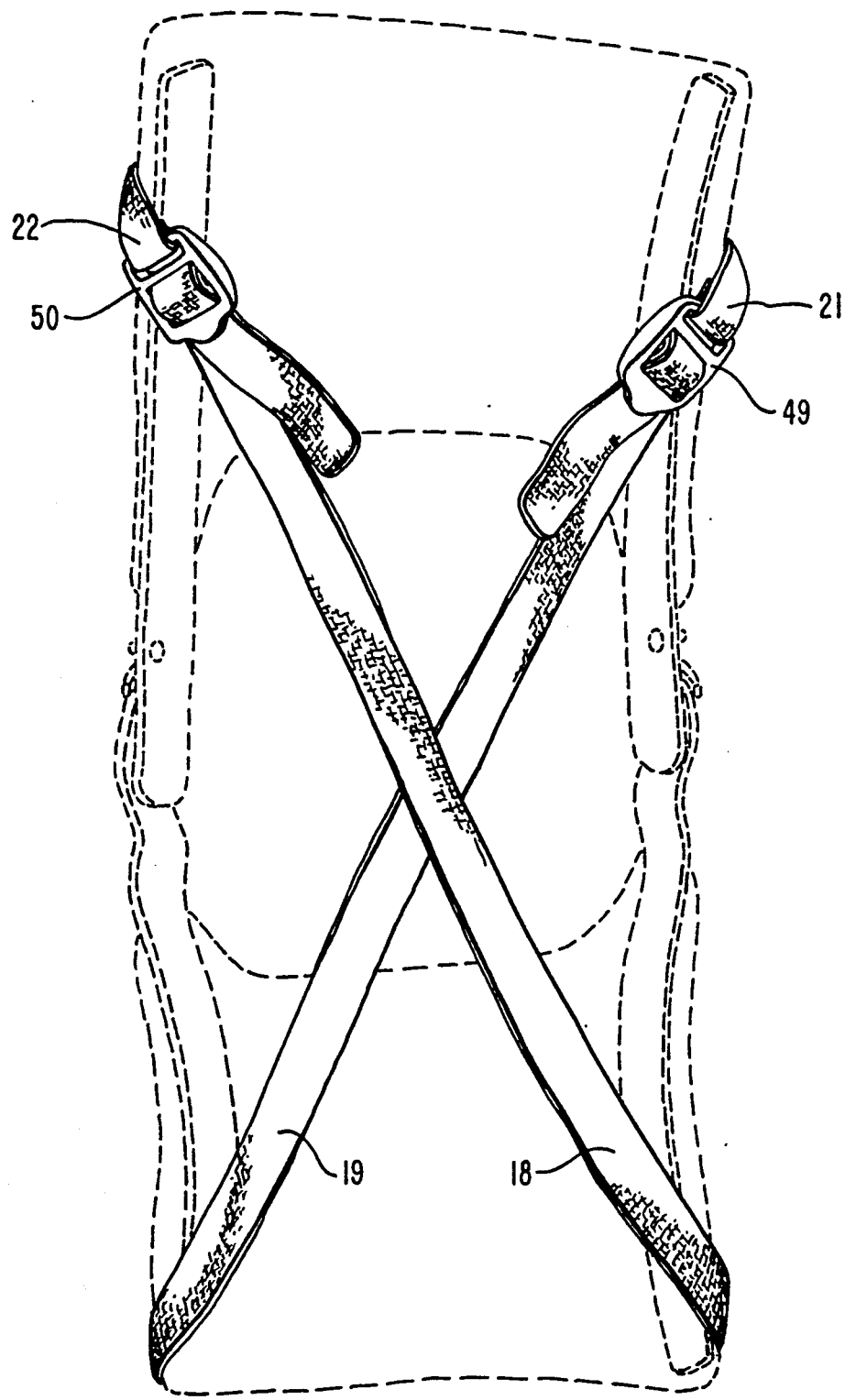
FIG. 4 is a rear view of a knee brace constructed in accordance with the principles of the present invention showing the crossing straps as they would be attached around the back of a user's leg.

As shown in FIG. 4, cross-straps 18 and 19 are adjusted to a predetermined length which will tend to pull upper cuff 11 and lower cuff 12 towards each other as the knee approaches a desired, predetermined limit of extension.

The intended functioning of the hinge and locking mechanism will now be explained. As best shown in FIGS. 6a, and 6b (from which we have omitted the immobilization bands and straps in order to allow for clarity in the explanation of the functioning of the cross-straps 18 and 19.) when the user's knee is bent, cross-straps 18 and 19 are slack and exert no force on the cuffs 11 or 12.

FIG. 6b, showing in schmetic form the brace 10 of FIG. 6a, includes member 67 which represents lower cuff 12 and lower hinge arm 14, and member 68 which represents upper cuff 11 and upper hinge arm 13. The gap (d) between member 67 and 68 is intended to represent the maximum separation distance between upper hinge arm 13 and lower hinge arm 14 allowed by the slots 24 and 25. Member 69 represents cross-straps 18 and 19.

As can be seen in FIG. 6b, since member 69 is slack, (carrying no tension therethrough). Member 67 and 68 are allowed to separate a distance (d) as the user rotates the knee through it's range of motion. Distance (d) remains constance until extension of the knee causes member 69 to be placed into tension. As is readily obvious, the degree of extension of the user's knee which causes element 69 to move into tension can be adjusted by adjusting the length of cross-straps 18 and 19.

As long as distance (d) remains at its greatest separation, the user may freely flex or extend the knee joint. Screws 34 and washer 31 "float" within the slots 24 and 25 as the knee joint rotates. This floating, freecentric motion of the hinging arms 13 and 14 relative to each other allows the hinge to effectively track the rotational motion of the knee.

As shown in FIG. 7a, as the knee joint is moved to it's extended position, cross-straps 18 and 19 eventually move into tension, and exert a tension force on the upper and lower cuffs 11 and 12. Since cross-straps 18 and 19 tend to pull upper and lower cuffs 11 and 12 towards each other, the distance (d) gradually decreases as the user continues to extend the knee joint.

As shown in 7b, due to the fixed length of element 69, the extension of the knee eventually causes elements 67 and 68 to be pulled together until distance (d) is zero. This position is the position at which slots 24 and 25 are oriented relative to each other such that further translational movement of cuff 11 towards cuff 12 is no longer possible. Also, this position, is the position in which hook 26 of lower hinge arm 14 is located high enough relative to upper hinge arm 13 that further extension of the user's knee will cause the semi-circular section 27 thereof to engage locking pin 23. Once brace 10 is finally forced into this locked position due to the tension caused by cross-straps 18 and 19 as the user extends the knee, further extension is prevented.

As can be readily discerned from the foregoing explanation, the user need merely adjust the length of cross-straps 18 and 19 to the correct length which will result in a locking of the hinge at the complete extension of the knee. The net effect of the hinging and locking mechanism of the present invention is that the hinge is free to track the motion of the knee without interference from the locking mechanism, until the cross-straps 18 and 19 move into tension and arrange (translate) the hook 26 and the locking pin 23 into proper position for engagement.

Figure 8:
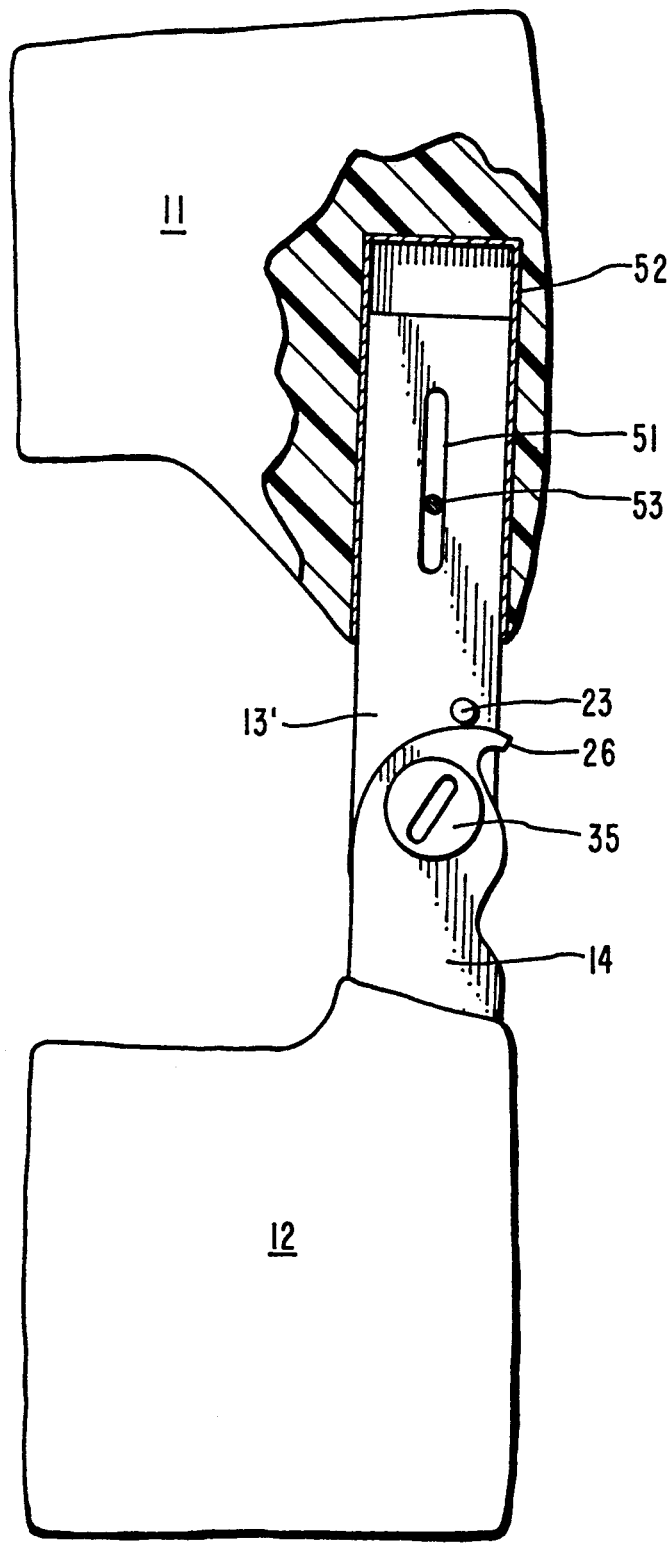
FIG. 8 is a partially cut away side view of a knee brace of the present invention employing a slidable hinge arm.

In FIG. 8, another embodiment of the present invention is shown. In this embodiment, upper hinge arm 13' may be attached to the cuff 11 in a freely slidably manner. This is accomplished by inserting a tubular casing 52 into the upper cuff 11, the tubular casing 52 being sized to allow free sliding movement of the upper hinge arm 13' therein. A free, or frictionless, sliding attachment between upper hinge arm 13' and cuff 11 allows for a much more secure attachment of the brace 10 to the user's leg. This is due to the fact that in use, the upper cuff 11 of the knee brace 10 generally tends to shift position along the user's thigh when the user flexes or extends the knee.

Generally, regardless of the amount or number of immobilization bands used to secure the upper cuff 11 to the user's leg, forces generated due to imperfect tracking of the hinge with the rotational motion of the knee, the cuff 11 is eventually forced out of its correct position on the thigh. Incorrect positioning of upper cuff 11 also can eventually cause the rest of the brace 10 to become mispositioned.

The free sliding upper hinge arm 13' of the present invention alleviates this problem by allowing a more perfect tracking of the hinge along the path of motion of the knee. The improvement in tracking of hinge arm 13' is due to its freely slidable attachment to the cuff 11 as the knee rotates in flexion, the center of rotation of the hinge must not only rotate in sync with the knee, but must also translate away from the fixed position of the cuff 11 on the user's thigh if it is to properly track the path of motion of the knee joint.

Although the upper hinge arm 13' is freely slidable relative to upper cuff 11, it is nevertheless secured in tubular chamber 52 by a pin 53 which passes through a slot 51 located centrally and longitudinally in the upper end of the hinge arm 13'. The pin 53 of course functions to prevent complete separation between the cuff 11 and the hinge arm 13'.

Figure 9:
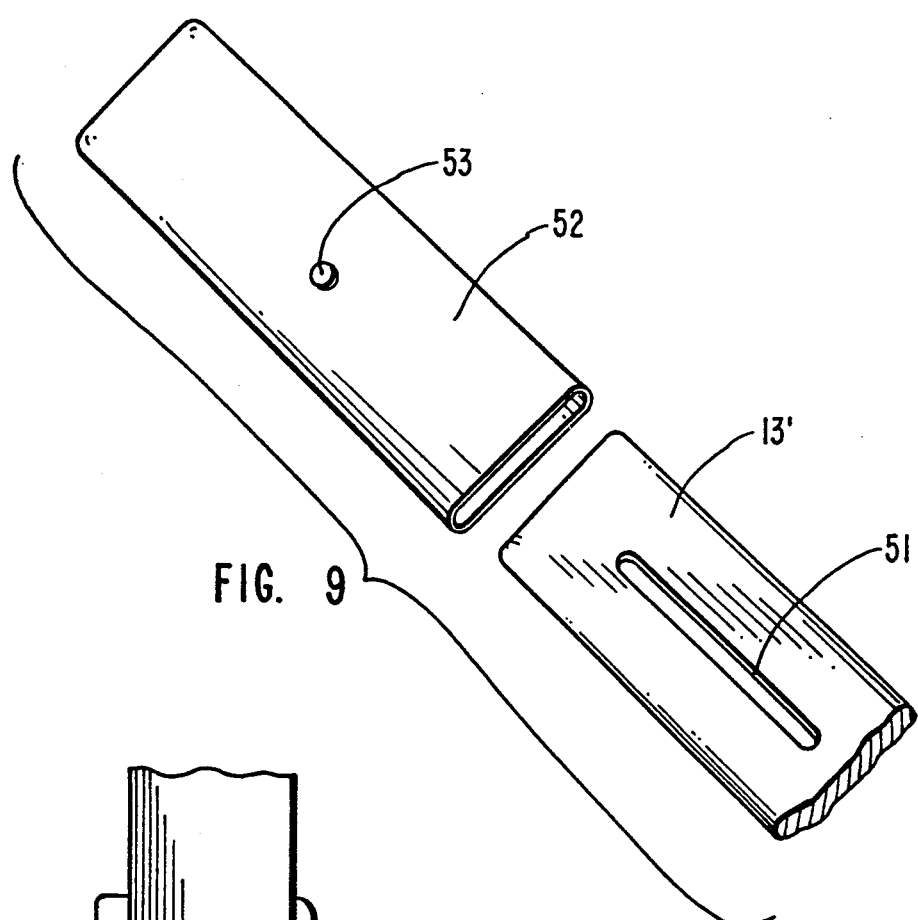
FIG. 9 is a perspective view of the hinge arm and tubular channel portions of the knee brace as shown in the alternative embodiment of FIG. 8.

As shown by FIG. 9, tubular casing 52 has an interior cross-sectional shape which is the same as the cross-sectional shape of the hinge arm 13'. The casing 52 may be formed of plastic, metal, fiberglass or any other suitable material. The hinge arm 13' is inserted into the casing 52, and then the pin 53 is passed through the casing 52 and slot 51. The casing is then formed into, or as a part of, the upper cuff 11.

Figure 10:
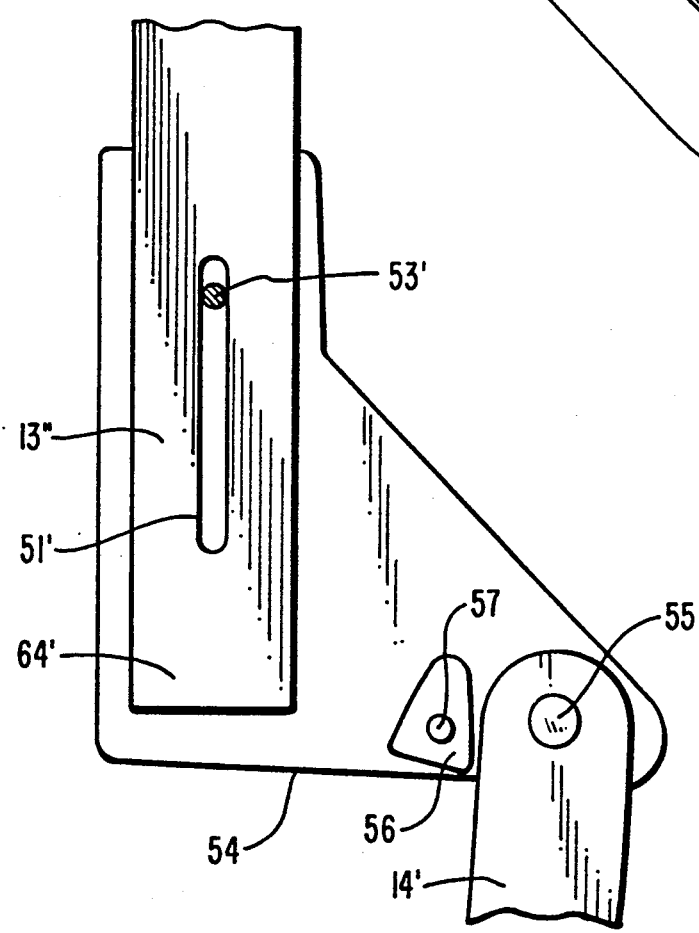
FIG. 10 shows an alternative hinge design employing the slidable upper hinge arm feature of the present invention, (the hinge having the top plate thereof removed for simplicity of illustration).

As shown by FIG. 10, the free sliding hinge arm concept may be employed in other prior art type knee braces if desired. Further in such prior art knee braces, the free sliding end of the upper hinge arm 13" may be located at the upper hinge arm's 13" attachment to the hinging elements as opposed to being located at the hinge arm's 13" attachment to the upper cuff 11. In this embodiment, distal end 64' of upper hinge arm 13" is attached to plate 54, which in fact constitutes the hinging portion of a prior art type knee brace. The plate 54 has an equivalent plate (not shown for purposes of clarity) which overlays plate 54 to complete the hinge.

Upper hinge arm 13" includes a slot 51' which runs longitudinally of the length of the upper hinge arm 13". Pin 53' is past through slot 51' and secured to plate 54 and its counterpart (not shown). The lower hinge arm 14' may be attached to plate 54 as by pin 55 in a conventional manner. Also, a locking wedge 56 may be attached to plate 54 by means of pin 57. Wedge 56 is oriented such that hyperextension of the user's knee is prevented when lower hinge arm 14' rotates and comes in contact therewith.

Although the preferred embodiments of the knee brace of the present invention have been illustrated and described, it is to be understood that the present disclosure is made by way of example and that various other embodiments are possible without departing from the subject matter coming within the scope of the following claims, which subject matter is regarded as part of the invention.

We claim:
1. A knee brace comprising:
   upper and lower cuff means for positioning said brace on a user's leg, said upper cuff means being positionable about the thigh area of the user's leg and said lower cuff means being positionable about the shin area of the user's leg, upper and lower hinge arm means for hingeably attaching said upper cuff means to said lower cuff means, said upper hinge arm means being attached to said upper cuff means and said lower hinge arm means being attached to said lower cuff means, said upper and lower hinge arm means being rotatably attached to each other by free-floating connector means which have a single hinge axis and which attach said upper hinge arm means to said lower hinge arm means in a manner which allows free rotation and translation of said upper hinge arm means relative to said lower hinge arm means, and which also allows relative rotation and translation of said free floating connector means relative to said upper and lower hinge arm means.

2. A knee brace according to claim 1 wherein said free floating connector means further allows said relative rotation of said upper hinge arm means relative to said upper hinge arm means to occur simultaneously with said relative translation of said upper hinge arm means relative to said lower hinge arm means.

3. A knee brace according to claim 1 wherein said upper hinge arm means is slideably attached to said upper cuff means, whereby, said upper hinge arm means is freely translatable relative to said upper cuff means.

4. A knee brace according to claim 3 wherein said free sliding connection of said upper hinge arm means with said upper cuff means includes an elongate tubular casing means which is securely held by said upper cuff means, said upper hinge arm means having an elongate channel means formed therein which defines a longitudinal axis corresponding to an axis of relative translation between said upper cuff means and said upper hinge arm means, said elongate channel means of said upper hinge arm means being located in said elongate tubular casing means, and held in place therein by a pin member which extends through said elongate channel means and is secured to said elongate tubular casing means, whereby, said relative translation of said upper cuff means relative to said upper hinge arm means is limited only by the range of motion allowed by said pin member in said elongate channel means.

5. A knee brace according to claim 1 wherein said hinge means further includes
an elongated slot located in said upper hinge arm means, and an elongated slot located in said lower hinge arm means, said free floating connector means being located through said elongated slots, whereby, relative translation of said upper hinge arms means relative to said lower hinge arms means is limited to the relative translational motion allowed by said free floating connector means in said slots.

6. A knee brace comprising:
upper and lower cuff means for positioning said brace on a user's leg, said upper cuff means being positionable about the thigh area of the user's leg and said lower cuff means being positionable about the shin area of the user's leg, upper and lower hinge arm means for hingeably attaching said upper cuff means to said lower cuff means, said upper hinge arm means being attached to said upper cuff means and said lower hinge arm means being attached to said lower cuff means, said upper and lower hinge arm means being rotatably attached to each other by free-floating connector means which attach said upper hinge arm means to said lower hinge arm means in a manner which allows rotation and translation of said upper hinge arm means relative to said lower hinge arm means, and which also allows relative rotation and translation of said free floating connector means relative to said upper and lower hinge arm means, wherein said free floating connector means further allows said relative rotation of said upper hinge arm means relative to said upper hinge arm means to occur simultaneously with said relative translation of said upper hinge arm means relative to said lower hinge arm means, locking means comprising a pin means located on said upper hinge arm means, and a hook means located on said lower hinge arm means, and means for engaging said hook means and said pin means at a predetermined extension position of the user's knee when said brace is properly positioned thereon.

7. A knee brace according to the claim 6 wherein said engaging means includes cross strap means, said cross strap means being attachable to said lower cuff means and said upper cuff means, and having an adjustable length, whereby, tension generated in said cross-strap means due to extension of the user's knee, forces said pin means and said hook means to translate towards each other into engageable position, and further extensional rotation of the knee causes the pin means and hook means which have been translated into engageable position due to forces generated by the cross strap means thereafter to become engaged and lock said upper hinge arm means in fixed position relative to said lower hinge arm means, thereby preventing further extensional rotation of the user's knee.

8. A knee brace comprising:
upper and lower cuff means for positioning said brace on a user's leg, said upper cuff means being positonable about the thigh area of the user'leg and said lower cuff means being positionable about the shin area of the user's leg, upper and lower hinge arm means for hingeably attaching said upper cuff means to said lower cuff means, said upper hinge arm means being attached to said upper cuff means and said lower hinge arm means being attached to said lower cuff means, said upper and lower hinge arm means being rotatably attached to each other by free-floating connector means which attach said upper hinge arm means to said lower hinge arm means in a manner which allows rotation and translation of said upper hinge arm means relative to said lower hinge arm means, and which also allows relative rotation and translation of said free floating connector means relative to said upper and lower hinge arm means, wherein said free floating connector means further allows said relative rotation of said upper hinge arm means relative to said upper hinge arm means to occur simultaneously with said relative translation of said upper hinge arm means relative to said lower hinge arm means, locking means comprising a pin means located on said upper hinge arm means, and a hook means located on said lower hinge arm means, means for engaging said hook means and said pin means at a predetermined extension position of the user's knee when said brace is properly positioned thereon, an elongated slot located in said upper hinge arm means, and an elongated slot located in said lower hinge arm means, with the longitudinal axis of the slots in said upper and lower hinge arm means forming an angle of approximately 90 degrees when said hook means and said pin means of said locking means are engaged in their locked position.

9. A slidable connection on a knee brace having an upper cuff means for positioning about the thigh area of a user, and an upper hinge arm means attached at one end thereof to the upper cuff means and at the opposite end thereof to a hinge means, the hinge means being located adjacent the user's thigh, the slidable connection comprising, elongate channel means located in said upper hinge arm means, and pin means fixed to said upper cuff means, said pin means passing through said elongate channel means, whereby, said upper hinge arm means is freely slidable relative to said upper cuff means through a range of motion limited only by the fixation of said pin means to said upper cuff means through said elongate channel means.

10. A slidable connection according to claim 9 further comprising tubular casing means fixed in said upper cuff means, said pin means being fixed in said tubular casing means, said upper hinge arm means being at least partially located in said tubular casing means due to the location of said pin means through said elongate channel, whereby rotational motion of said upper hinge arm means relative to said upper cuff means is restricted, while translational motion of said upper hinge arm means relative to said upper cuff means remains uninhibited.

11. A knee brace comprising:

an upper cuff means for positioning about the thigh area of a user, an upper hinge arm means attached at one end thereof to the upper cuff means and at the opposite end thereof to a hinge plate that is located adjacent the user's knee when the upper cuff means is attached to the user's thigh, a lower cuff means for positioning about the shin area of a user's leg, a lower hinge arm means attached at one end to said lower cuff means, with the opposite end thereof being hingeably attached to said hinge plate for rotational movement about a hinge axis on said hinge plate, elongate channel means associated with said upper hinge arm means and said hinge plate, an elongate channel means in said upper hinge arm means, and pin means fixed to said hinge plate and elongate channel and spaced laterally from said hinge axis, with said pin means passing through said elongate channel means, whereby, said upper hinge arm means is freely slidable along the elongate channel means relative to said hinge plate means through a range of motion limited only by the fixation of said pin means to said hinge means through said elongate channel means.

* * * * *

UNITED STATES PATENT AND TRADEMARK OFFICE
CERTIFICATE OF CORRECTION

PATENT NO. : 5,063,916
DATED : November 12, 1991
INVENTOR(S) : E. Paul France et al.

It is certified that error appears in the above-identified patent and that said Letters Patent is hereby corrected as shown below:

In column 10, line 39, please delete "user'leg" and insert therefor -- user's leg --.

In column 11, line 13, after "located adjacent the" please insert -- user's knee when the upper cuff means is attached to the --.

In column 12, line 8, after "adjacent", please insert -- to --.

In column 12, line 20, please delete "channel means" and insert therefor -- slot --.

Signed and Sealed this

Twenty-eighth Day of June, 1994

Attest:

BRUCE LEHMAN

*Attesting Officer*        *Commissioner of Patents and Trademarks*